United States Patent [19]

Tam et al.

[11] 4,274,419
[45] Jun. 23, 1981

[54] SKIN PREPARATION DEVICE AND METHOD USED IN THE APPLICATION OF MEDICAL ELECTRODES

[75] Inventors: Hak W. Tam, Kirkland; Vernon E. Modes, Kent, both of Wash.

[73] Assignee: Quinton Instrument Co., Seattle, Wash.

[21] Appl. No.: 86,590

[22] Filed: Oct. 19, 1979

[51] Int. Cl.³ .................................................. A61B 5/04
[52] U.S. Cl. ...................................... 128/639; 128/734
[58] Field of Search .............................. 128/639–641, 128/644, 783, 798, 802, 803, 734, 303 R, 303.1

[56] References Cited

U.S. PATENT DOCUMENTS

| | | | |
|---|---|---|---|
| 2,887,112 | 5/1959 | Smith | 128/644 |
| 3,774,592 | 11/1973 | Lahr | 128/640 |
| 3,911,906 | 10/1975 | Reinhold, Jr. | 128/641 |
| 4,027,664 | 6/1977 | Heavner, Jr. et al. | 128/641 |
| 4,126,126 | 11/1978 | Bare et al. | 128/639 |

OTHER PUBLICATIONS

Tam et al., "Minimizing Electrode Motion Artifact . . . ", IEEE Trans. on Bio. Med. Eng., vol. 24, No. 2, Mar. 1977, 134–139.
Burbank et al., "Reducing Skin Potential Motion Artifact . . . ", Med. and Biol. Eng. and Comput., 1978, 16, 31–38.

*Primary Examiner*—Lee S. Cohen
*Attorney, Agent, or Firm*—Seed, Berry, Vernon & Baynham

[57] ABSTRACT

A method and device for preparing the skin of a patient to ensure good electrical contact between a medical electrode and the patient's skin. The electrode or the tips of the preparation device includes an abrasive pad impregnated with an electrolyte for providing good electrical contact with the patient's skin. When an electrode is used, the pad is centrally mounted and is rotated in a housing having an adhesive annular rim which is secured to the skin. The pad is rotatably driven by the preparation device which continuously measures the impedance between the pad of the electrode and a reference electrode, which is also secured to the skin. A motor in the preparation device rotates the pad to abrade the skin responsive to actuation of a switch. Rotation of the pad terminates within a predetermined period or when the impedance between the pad and reference electrode falls to a predetermined value, whichever occurs first. The impedance between the electrode being applied and the reference electrode is measured by producing an alternating current having a constant magnitude between the electrodes, rectifying the voltage across the electrodes, which is proportional to the impedance therebetween and the voltage, to an adjustable reference voltage. When the rectified voltage drops to the reference voltage a manually actuated timer powering the motor is reset if the timer has not already been reset after the predetermined period.

17 Claims, 3 Drawing Figures

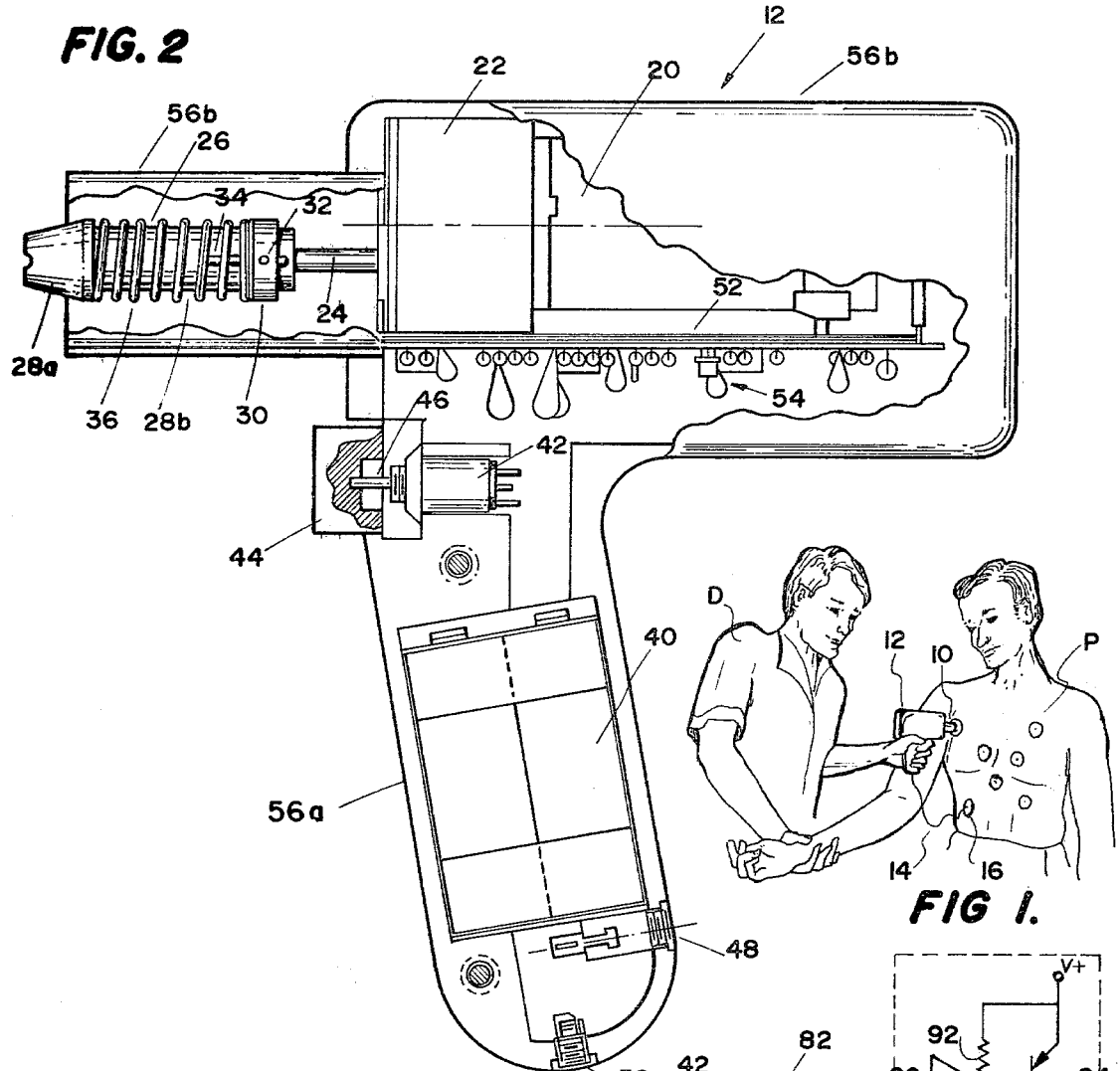
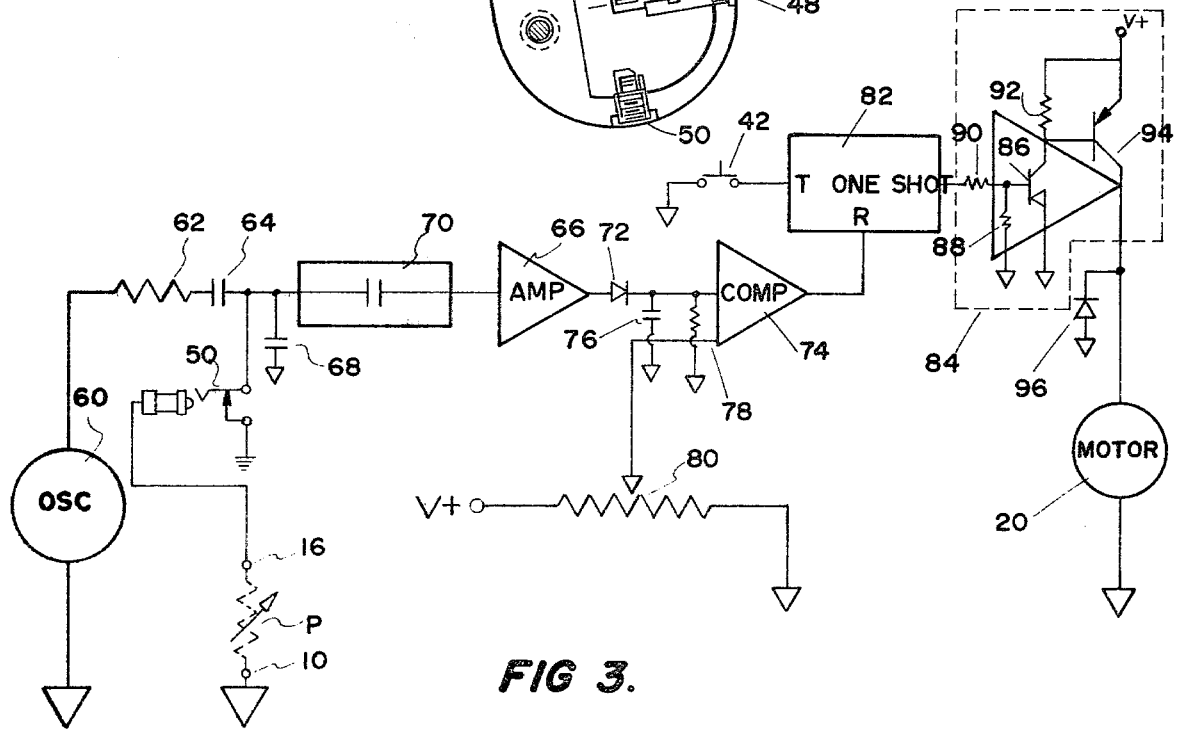

SKIN PREPARATION DEVICE AND METHOD USED IN THE APPLICATION OF MEDICAL ELECTRODES

BACKGROUND OF THE INVENTION

1. Field of the Invention

This invention relates to the preparation of a patient's skin to ensure good electrical contact with a medical electrode, and more particularly to a device for automatically abrading the skin until the impedance at the interface between the skin and the abrading means drops to a predetermined value.

2. Description of the Prior Art

Medical electrodes are commonly used to perform a large number of medical tests, such as electrocardiograms. These electrodes are generally of the disposable variety having an electrolyte-impregnated pad surrounded by a housing which is adhesively secured to the skin. In order for the electrode to properly sense subcutaneous electrical signals, the skin of the patient must be prepared by abrading the skin on which the electrode is to be placed. This abrasion removes foreign matter and a layer of dead skin to ensure better electrical contact between the electrolyte pad and the patient's skin.

Skin preparation for medical electrodes is presently accomplished by manually rubbing the patient's skin with a pad containing a cleansing agent. The primary disadvantages of this technique are the length of time required to prepare the patient for a medical test utilizing medical electrodes and the inability to precisely control the degree of skin preparation. In many medical tests, such as an electrocardiogram, a large number of electrodes—on the order of 3 to 14—must be secured to the patient's skin. Preparation of the patient's skin by manual means requires a great deal of time, thereby making such tests fairly costly. Manual preparation of the skin is continued until it appears to the person applying the electrodes that the skin has been abraded sufficiently. However, since this visual technique is rather imprecise, skin abrasion is either insufficient to allow the electrode to accurately receive voltage levels or excessive, causing patient discomfort.

A new type medical electrode is described in copending application, Ser. No. 003,109, filed Jan. 15, 1979, and entitled "MEDICAL ELECTRODE AND SYSTEM FOR MINIMIZING MOTION ARTIFACTS". This medical electrode includes an abrasive pad impregnated with an electrolyte solution which is rotatably mounted in a cylindrical housing. The housing is surrounded by an annular rim having an adhesive coating securing the electrodes to the skin. Skin preparation is easily and quickly accomplished by rotating the pad against the skin of the patient after the electrode has been secured to the skin. One problem associated with use of the above-described electrode is the difficulty in determining when the skin has been sufficiently prepared. The pad of the electrode may be rotated manually to abrade the skin or preferably be rotated by power means such as an electric motor. Individual patients require different amounts of preparation because of their differing skin characteristics; thus, a constant amount of skin preparation by the abrasive pad of the electrode may be excessive in some cases and insufficient in others.

SUMMARY OF THE INVENTION

The basic object of this invention is to quickly, easily and safely apply a large number of medical electrodes of the type described to the skin of a patient in a manner which ensures adequate and uniform skin preparation for each applied electrode.

It is another object of the invention to provide a skin preparation device for abrading the skin of a patient through an abrasive gel-impregnated pad only until a specific degree of skin preparation has been accomplished.

It is still another object of the invention to provide a method and device for continuously measuring the degree of skin preparation during the skin preparation procedure prior to or during application of medical monitoring electrodes.

These and other objects of the invention are provided by continuously measuring the impedance of the interface between an abrasive pad attached to a preparation device or the sensing means of a monitoring electrode and the skin of the patient during skin preparation relative to an applied reference electrode. This is accomplished by first applying a reference electrode to the skin after adequate skin preparation, either by manual means or mechanized preparation where the electrode has a rotatably mounted pad as described in the above-mentioned co-pending application. Secondly, the skin where the electrodes are to be applied is abraded with an abrasive pad secured to the tip of the preparation device or impregnated with electrolyte and a large number of monitoring electrodes are applied to the skin of the patient with the sensing element of each of the monitoring electrodes moved relative to the skin in contact with the sensing element by the skin preparation device while the impedance between the abrading tip or sensing element and the reference electrode is continuously measured. When the impedance falls to a predetermined value, further abrasion of the skin by the device is terminated. The impedance measurements are accomplished by generating an alternating current having a constant magnitude between the reference electrode and the monitoring electrode being applied and measuring the voltage across the electrodes, the voltage being proportional to the impedance. The voltage is then rectified and compared with a manually adjustable reference voltage. When the impedance voltage at the interface between the monitoring electrode and skin falls to the level of that of the reference voltage, power is removed from the electric motor of the skin preparation device used to abrade the skin. The skin preparation device also includes a circuit for creating a low impedance relative to the impedance at the interface between the monitoring electrode and skin if the reference leadwire is not connected to the skin preparation device. A high pass filter is preferably positioned between the reference electrode and the rectifier for preventing DC voltages generated by the reference electrode and monitoring electrode being applied from interfering with the impedence measurements. As an additional safety feature to prevent excessive skin preparation, rotation of the motor of the skin preparation device may be terminated after a predetermined time period if the impedance at the interface between the monitoring electrode and skin has not fallen to the preset value.

BRIEF DESCRIPTION OF THE DRAWINGS

FIG. 1 is an isometric view of the skin preparation device as used on a patient in preparing the skin of the patient by abrading the skin of the patient beneath the sensing element of the monitoring electrode.

FIG. 2 is a side elevational view of the skin preparation device for use with a medical electrode capable of preparing the skin of a patient after application thereof.

FIG. 3 is a schematic of the circuit used in the skin preparation device of FIG. 2.

DETAILED DESCRIPTION OF THE INVENTION

As illustrated in FIG. 1, a medical monitoring electrode 10 of the type having means to abrade the skin of the patient is secured to a patient P, and the skin beneath the sensing element of the electrode 10 is prepared by a medical technician utilizing the skin preparation device 12. The monitoring electrode may be of the type disclosed in patent application Ser. No. 003,109 (previously mentioned), the disclosure of which is hereby incorporated by reference, or an electrode of other design having means to prepare the skin of the patient contacted by the sensing element of the electrode after the electrode is secured to the patient. A leadwire 14 extends from the device 12 to a reference electrode 16 which has been previously secured to the patient P after the patient's skin has been prepared. If the reference electrode 16 is of the conventional type, the skin beneath the electrode 16 is prepared utilizing the conventional manual technique. If the reference electrode 16 is of the rotatable abrasive pad variety described in patent application Ser. No. 003,109, the skin is prepared by abrading the skin with the rotating pad either manually or by power means for a predetermined period. The device 12 rotates the rotatably mounted pad of the electrode 10 while continuously measuring the impedance between the electrode 10 and the reference electrode 16. When the electrode 10 is initially applied to the patient's skin, the impedance is relatively high, primarily due to a surface layer of dead skin contacting the pad of the electrode 10. As this layer of dead skin is abraded by rotation of the pad, the impedance is reduced. The device 12 includes means for determining when the impedance is lowered to a preset level, at which time rotation of the pad of the electrode 10 is terminated.

The skin preparation device for rotating the rotatably mounted abrasive pad of the medical electrode is illustrated in greater detail in FIG. 2. The device 12 includes a conventional DC motor 20 with electrically conductive housing and shaft which may be, for example a 3-Amp, 4.8 volt motor manufactured by the Barber-Colman Company of Rodeford, Illinois, which spins at about 3,800 RPM at 18 inch-ounce load condition. The motor 20 drives a conventional reduction gear assembly 22 which may have a reduction ratio, for example, of about 8.33:1. The reduction gear assembly 22 includes an output shaft 24 on which an electrically conductive drive assembly 26 is mounted. The drive assembly 26 is connected to one terminal of the impedance sensing circuit so that skin impedance can be measured through electrode 10 as it rotates the pad of the electrode. The drive assembly 26 includes a drive member 28 having a drive head 28a and an integral cylindrical portion 28b of smaller diameter than the drive head 28a slidably mounted on the output shaft 24. An annular collar 30 of larger diameter than the cylindrical portion 28b surrounds the cylindrical portion 28b and is retained on the output shaft 24 by a spoke 32 which extends through a slot 34 formed in the cylindrical portion 28b of the drive member 28. The drive member 28 is freely slidable on the output shaft 24 in an axial direction. A compression spring 36 extends between the drive head 28a and the collar 30 to resiliently bias the drive head 28a in an axial direction away from the collar 30. This resilient biasing allows the drive head 28a to exert a predetermined, relatively constant pressure on the abrasive pad of the electrode being applied to the patient as it rotates the pad. The drive assembly 26 also furnishes a electrically conductive path for continuous impedance sensing purpose.

Power is initially applied to the motor 20 by a battery pack 40 when a conventional switch 42 is closed by depressing a trigger 44 carried by an actuating shaft 46 projecting from the switch 42. The battery pack 40 is preferably composed of rechargeable batteries which are charged by a conventional battery charger connected to the battery pack 40 through a conventional charging jack 48. A second jack 50 is provided to receive the leadwire 14 (FIG. 1) extending from the reference electrode 16 and functioning as a leadwire sentry circuit. The jack 50 is preferably of the type commonly used with small radios and tape recorders for receiving an earphone plug. Jacks of this type automatically disconnect the audio output from a loudspeaker and instead apply it to the earphone. As explained in greater detail hereinafter, when a plug is not inserted in the jack 50 the impedance measuring circuitry receives a signal indicative of an extremely low impedance so that the motor 20 does not rotate. When a plug is inserted into the jack 50, the impedance measuring circuitry receives a signal indicative of the actual impedance between the electrode 10 and the reference electrode 16. Operation of the skin preparation device is thus prevented unless the reference electrode plug has been inserted in the jack 50. The above described leadwire sentry circuit reduces the risk of operator error as well as conserving battery power when the device is inadvertently triggered without the reference wire attached.

The circuitry for measuring impedance and controlling the operation of the motor 20 is mounted on a printed-circuit board 52 with the circuit components, indicated generally at 54, pointing downwardly as illustrated in FIG. 2.

All of the above-described components of the skin preparation device 12 are mounted in a housing having a pistol grip handle portion 56a, a motor and circuit enclosure 56b and a drive assembly enclosure 56c which is preferably fabricated from a transparent material. The housing is preferably formed using a durable, insulating material.

The circuitry for measuring impedance and controlling the operation of the motor 20, generally indicated at 54 in FIG. 2, is shown schematically in FIG. 3. An AC signal is generated by a conventional oscillator 60 and applied to the jack 50 through a relatively high impedance resistor 62 and a DC blocking capacitor 64. The frequency of the oscillation is preferably about 55 Hz to minimize interference from extraneous AC power signals which are either 50 to 60 Hz for most countries. The resistor 62 preferably has a resistance which is substantially greater than the maximum impedance through the body of the patient between the reference electrode 16 and the applied electrode 10. When the electrode 10 is initially applied to the patient's skin, the impedance between the electrode 16 and electrode 10 (it being remembered that the conductive drive head 28a (FIG. 1) electrically conducts between the electrode 10 and one terminal of this impedance sensing circuit whereas the reference wire 14, attached to electrode 16, electrically conducts between electrode 16 and the other terminal of the impedance sensing circuit) is generally between 50,000 ohms and 200,000 ohms. When the skin of the patient beneath the electrode 10 has been properly prepared, however, the impedance between the electrodes 10 and 16 drops to about 3,500 ohms. By making the impedance of resistor 62 substantially larger than 200,000 ohms—on the order of 1 megaohm—the current through the patient is relatively insensitive to variations in the interelectrode impedance. The oscillator 60 and resistor 62 thus function as a non-polarizating constant.

The medical electrode 10, as with other types of electrodes, generates a DC potential which may interfere with proper impedence measurements. These DC potentials are elimnated by the blocking capacitor 64.

Since the current between the electrodes 16 and 10 is constant, the voltage at the reference electrode 16 is directly proportional to the impedance between the electrodes and this impedance is indicative of the impedance at the interface between the electrode 10 and the skin of the patient. This voltage is applied to a conventional voltage amplifier 66 through a wide band pass filter formed by capacitors 68 and 70. Capacitor 68 attenuates noise signals having frequency components far in excess of 55 Hz, while capacitor 70 attenuates relatively low frequency signals and DC potentials generated by the electrodes 16 and 10. The output of amplifier 66 is half-wave rectified by a diode 72 to produce a DC voltage which is indicative of the impedance of the skin/electrode 10 interface. This DC voltage is applied to one terminal of a conventional voltage comparator 74 which is low pass filtered by capacitor 76 and resistor 78. Capacitor 76 causes the input to the comparator 74 to be relatively constant even though current flows through the diode 72 for only a small portion of each AC cycle. Resistor 78 provides a discharge path to ground so as to slowly discharge the capacitor 76. The other input to comparator 74 is a DC reference voltage from the wiper of a potentiometer 80 which is connected between a supply voltage and ground to form a voltage divider. The wiper of the potentiometer 80 is manually adjustable to select a predetermined impedance point at which the output of the comparator 74 switches. The output of the comparator 74 is applied to the reset terminal of a conventional one-shot or timer 82. The trigger input to the one-shot 82 is selectively grounded by the switch 42 of FIG. 2. When the switch 42 is actuated, the one-shot 82 drives a current amplifier 84 causing current to flow through the motor 20 to rotate the rotatably mounted pad of the electrode 10. After a predetermined period, as set by the internal components of the one-shot 82, the output of the one-shot 82 falls to 0 volts, causing the current amplifier 84 to cut off power to the motor 20. If the impedance between the electrodes 16 and 10 falls to the reference level set by the potentiometer 80 before the end of this predetermined period, the one-shot 82 is reset to cause the current amplifier 84 to cut off power to the motor 20.

The current amplifier 84 includes a first transistor 86 which is normally biased "off" through resistor 88. When the one-shot 82 is triggered, a positive voltage is applied to the base of transistor 86 through resistor 90 causing current to flow through resistor 92 and the base-emitter junction of transistor 86. A second transistor 94, normally biased "off" by resistor 92, is then turned "on" by the voltage drop across resistor 92, causing current to flow through the emitter-collector junction of transistor 94 and the motor 20. A reverse biased diode 96 is connected between the motor 20 and ground to shunt transients to ground which are generated by the motor 20 in order to protect the transistor 94.

In operation the individual D applying the electrodes applies the reference electrode 16 and the electrode 10 to the patient as described above. The individual D then places the drive head 28a of the preparation device 12 against the cup for the abrasive, electrolyte-impregnated pad which is rotatably mounted in the housing of electrode 10. The device 12 is urged against the electrode 10 with sufficient axial force to compress the coil spring 36 so that the pressure of the device 12 against the electrode 10 is relatively constant during the preparation procedure. The AC signal from the oscillator 60 is applied to the reference electrode 16, causing a contant current to flow to ground through the reference electrode 16, patient P, electrode 10 and the drive member 28. An AC signal having a peak amplitude, which is proportional to the impedance between the electrodes 16 and 10, is thus generated at the output of amplifier 66 and rectified by diode 72 to produce a DC voltage indicative of the impedance at the skin/electrode 10 interface. The individual D then manually actuates switch 42 to trigger the one-shot 82 and cause the current amplifier 84 to apply power to the motor 20. Since the motor 20 has not yet begun to rotate, the rotatably mounted pad, the initial impedance between the electrodes 10 and 16 is relatively high so that the voltage applied to the first terminal of the comparator 74 is substantially greater than the reference voltage from the potentiometer 80. Rotation of the motor 20 rotates the pad in the electrode 10 to abrade skin beneath the electrode 10, thereby causing the impedance at the interface between the skin and electrode 10 to continually decrease. When this impedance drops to a level corresponding to the reference voltage from potentiometer 80, the one-shot 82 is reset causing the current amplifier 84 to cut off power to the motor 20. Rotation of the abrasive pad of the electrode 10 is thus terminated. The preparation device 12 is then used to prepare the skin beneath another applied electrode. If, for some reason, the impedance of the skin/electrode interface does not fall to the value preset by the potentiometer 80 within a predetermined period, the internal circuit components of the one-shot 82 cause it to reset after a predetermined duration, thereby causing the current amplifier 84 to cut off power to the motor. Thus, abrasion of the skin beneath the electrode 10 automatically terminates before the skin of the patient is excessively abraded.

If the individual D fails to insert a plug connected to the reference electrode 16 into jack 50, the lead from the jack 50 is connected to ground. Consequently, the voltage applied to amplifier 66 is zero, so that the voltage applied to the first terminal of the comparator 74 is less than the voltage reference from potentiometer 80. Under these circumstances the one-shot 82 is reset as soon as it is triggered, so that rotation of the motor 20 is prevented.

The preparation device described enables quick and easy preparation of the skin beneath the medical electrode 10. The skin preparation is, in every case, uniform and sufficient to provide proper electrical contact beteen the electrode 10 and the patient without excessive skin abrasion.

We claim:

1. A method of preparing the skin of a patient to provide proper electrical contact between the skin and a medical electrode to be secured to the skin of the patient, comprising:

applying a reference electrode to a prepared site on the skin of the patient;

abrading an unprepared site on the skin of the patient with an abrasive pad impregnated with an electrolyte;

measuring the difference of the impedance between the abrasive pad and the reference electrode during abrading of the skin with the abrasive pad; and terminating abrasion with the abrasive pad when the difference of the impedance between the abrasive pad and the reference electrode reaches a preset value.

2. A method of preparing the skin of a patient to provide proper electrical contact between the skin and a monitoring medical electrode, comprising:

applying a reference electrode to a previously prepared site on the skin of the patient, the reference electrode having means establishing an electrical connection between the prepared site on the skin and the reference electrode for sensing and conveying bioelectric signals;

applying a monitoring electrode to an unprepared site on the skin of the patient, the monitoring electrode having electrically conductive means for sensing and conveying bioelectric signals, the electrically conductive means including abrading means in contact with the skin for abrading the portion of the skin in contact therewith;

abrading the portion of the skin contacted by the abrading means of the monitoring electrode;

measuring the relative difference in impedance at the abrading means/skin interface relative to the impedance at the reference electrode/skin interface during abrading of the skin with the abrading means; and terminating abrasion of the skin with the abrading means when the difference in impedance between the abrading means/skin interface and reference electrode/skin interface falls to a preset value.

3. A method of preparing the skin of a patient to provide proper electrical contact between the skin and a monitoring medical electrode, the monitoring electrode having electrically conductive means for sensing and conveying bioelectric signals, including an abrasive pad impregnated with an electrolyte mounted for rotation in contact with the skin of the patient after application of the monitoring electrode to the skin, comprising:

applying a reference electrode to a previously prepared site on the skin of the patient, the reference electrode having electrically conductive means in contact with the prepared site on the skin of the patient for sensing and conveying bioelectric signals;

applying a monitoring electrode to an unprepared site on the skin of the patient with the electrolyte-impregnated abrasive pad in contact with the unprepared skin of the patient;

rotating the abrasive pad of the monitoring electrode;

continuously measuring the relative difference of the impedance at the abrasive pad/skin interface of the monitoring electrode relative to the impedance at the electrically conductive means/skin interface of the reference electrode during rotation of the abrasive pad; and terminating rotation of the abrasive pad when the relative difference in the impedance between the abrasive pad/skin interface and electrically conductive means/skin interface falls to a preset value.

4. The method of claim 3, wherein the AC impedance between the monitoring electrode and reference electrode is measured such that DC potentials generated by the monitoring electrode and reference electrode do not affect the impedance measurements.

5. The method of claim 4, wherein the impedance measurements are accomplished by the steps of generating an alternating current having a constant magnitude between the monitoring electrode and reference electrode and measuring the voltage across the monitoring electrode and reference electrode.

6. The method of claim 5, wherein the alternating current is of a magnitude and frequency that avoids physiological changes or responses of the skin tissue.

7. The method of claim 3, further including the step of terminating rotation of the abrasive pad of the monitoring electrode after a predetermined period regardless of whether the impedance between the monitoring electrode and reference electrode has fallen to the preset value in order to prevent excessive abrasion of the skin in the event of an improper impedance measurement.

8. An apparatus for preparing the skin of a patient to provide proper electrical contact between the skin and an abrasive pad impregnated with an electrolyte in contact with and movable relative to the skin of the patient, comprising:

an electrically conductive drive member for moving the abrasive pad relative to the skin of the patient to abrade the portion of the skin in contact with the abrasive pad;

means for completing an electrical circuit between the abrasive pad and the patient through the electrically conductive drive member, the means including a reference electrode having means establishing an electrical connection between a prepared site on the skin of the patient and the reference electrode; and impedance measuring means for measuring the relative difference of the impedance at the abrasive pad/skin interface and the electrical connection means/skin interface of the reference electrode, the electrically conductive drive member moving the abrasive pad to reduce the impedance at the abrasive pad/skin interface until such impedance falls to a preset reference value relative to the impedance at the electrical connection means/skin interface of the reference electrode.

9. An apparatus for preparing the skin of a patient to provide electrical contact between the skin and a monitoring medical electrode secured to the skin, the electrode including an abrasive pad impregnated with an electrolyte in contact with and movable relative to the skin of the patient for sensing and conveying bioelectric signals, comprising:

an electrically conductive drive member adapted to be electrically connected to the electrolyte-impregnated abrasive pad of the monitoring electrode to move the abrasive pad of the electrode relative to the skin of the patient;

an electric motor having an output shaft connected to the drive member for rotating the abrasive pad;

impedance measuring means for measuring the impedance between the drive member and a reference electrode having conductive means establishing an electrical connection between a prepared site on the skin of the patient and the reference electrode, the reference electrode electrically connected to the drive member so that the measurement of the relative impedance between the drive member and reference electrode provides an indication of the impedance at the abrasive pad/skin interface of the monitoring electrode;

initiating means for causing the motor to move the drive member when electrically connected to the monitoring electrode;

comparator means for generating a terminating signal when the impedance, as measured by the impedance measuring means, falls to the preset reference value; and control means for preventing the motor from continuing to move the drive member responsive to the terminating signal.

10. The apparatus of claim 9, wherein the drive member includes means for maintaining the pressure of the pad against the skin of said patient relatively constant.

11. The apparatus of claim 9, wherein the shaft of the motor functions as an electrically conductive path.

12. The apparatus of claim 9, wherein the impedance measuring means includes a constant current source connected in series with the drive member and electrically connectable to the reference electrode and voltage measuring means for measuring the voltage between the monitoring electrode electrically connectable to drive member and the reference electrode.

13. The apparatus of claim 9, including an electric plug to which the reference electrode is connectable to the impedance measuring means, the electrical plug including means for mating with an electric jack, the jack having a first terminal connected to a second terminal when the plug is not inserted in the jack, and which is connected to the plug and electrically isolated from the second terminal when the plug is inserted in the jack, the second terminal being connected to the drive member through a relatively low impedance path so that the motor is prevented from moving the pad of the monitoring electrode when the reference electrode is not connected to the impedance measuring means.

14. The apparatus of claim 9, wherein the impedance mesuring means includes an oscillator for generating an AC signal between the monitoring electrode connectable to the drive member and the reference electrode through an impedance sufficiently large so that the current flowing between the monitoring and reference electrode is insensitive to variations in the impedance at the interface between the abrasive pad of the monitoring electrode and the skin of the patient, and the voltage between the drive member and the reference electrode is indicative of the impedance at the interface between the skin/abrasive pad interface.

15. The apparatus of claim 9, wherein the impedance measuring means, comparator means and control means comprise:

a circuit element having an impedance which is substantially greater than the maximum impedance between the drive member and the reference electrode;

an oscillator for generating an AC signal between the monitoring electrode connectable to the drive member and the reference electrode through the circuit element;

a rectifier receiving a voltage from the reference electrode for producing an DC voltage which is proportional to the impedance between the reference electrode and the monitoring electrode connectable to the drive member;

a comparator receiving the output of the rectifier, the comparator generating a terminate signal when the DC voltage from the rectifier falls to a preset level;

manually controllable means for generating an initiate signal;

timer means for generating an actuate signal responsive to the initiate signal, the actuate signal continuing for a predetermined period or until the termination signal is generated by the comparator, whichever occurs first; and power circuit means operatively connected to the motor for applying power to the motor responsive to the initiate signal.

16. The apparatus of claim 15, further including a high pass filter positioned between the reference electrode and the rectifier for preventing DC voltages generated by the monitoring electrode and the reference electrode from interfering with the impedance measurements.

17. The apparatus of claim 9, including a housing containing the electrically conductive drive member, electric motor, measuring means, initiating means, comparator means, and control means, the housing having a piston grip configuration for ease of use.

* * * * *